US011285095B2

(12) United States Patent
Ahnfeldt et al.

(10) Patent No.: US 11,285,095 B2
(45) Date of Patent: *Mar. 29, 2022

(54) HAIR OILS FOR CONDITIONING KERATIN FIBRES

(71) Applicant: Henkel AG & Co. KGaA, Duesseldorf (DE)

(72) Inventors: Tina Ahnfeldt, Hamburg (DE); Sylvia Kerl, Boenningstedt (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/685,330

(22) Filed: Nov. 15, 2019

(65) Prior Publication Data

US 2020/0188284 A1 Jun. 18, 2020

(30) Foreign Application Priority Data

Dec. 17, 2018 (DE) ...................... 10 2018 221 937.0

(51) Int. Cl.
| | |
|---|---|
| A61K 8/88 | (2006.01) |
| A61K 8/31 | (2006.01) |
| A61K 8/34 | (2006.01) |
| A61K 8/37 | (2006.01) |
| A61K 8/92 | (2006.01) |
| A61Q 5/12 | (2006.01) |

(52) U.S. Cl.
CPC .................. *A61K 8/88* (2013.01); *A61K 8/31* (2013.01); *A61K 8/342* (2013.01); *A61K 8/37* (2013.01); *A61K 8/375* (2013.01); *A61K 8/922* (2013.01); *A61Q 5/12* (2013.01); *A61K 2800/59* (2013.01)

(58) Field of Classification Search
None
See application file for complete search history.

(56) References Cited

U.S. PATENT DOCUMENTS

| | | | | | |
|---|---|---|---|---|---|
| 6,086,903 | A | * | 7/2000 | Trinh | A61K 8/02 424/401 |
| 2004/0241200 | A1 | * | 12/2004 | Winn | A61Q 19/00 424/401 |
| 2010/0068162 | A1 | * | 3/2010 | Greenberg | A61K 8/31 424/59 |
| 2011/0268684 | A1 | | 11/2011 | Battermann et al. | |
| 2017/0112738 | A1 | * | 4/2017 | Delowsky | A61Q 5/004 |

FOREIGN PATENT DOCUMENTS

| | | | | |
|---|---|---|---|---|
| CN | 106491392 | A * | 3/2017 | |
| EP | 2623088 | A2 | 8/2013 | |
| GB | 1117129 | A * | 6/1968 | ............... A61Q 5/06 |
| WO | WO-2010019939 | A1 * | 2/2010 | ............. C07C 67/08 |
| WO | 2010063565 | A1 | 6/2010 | |
| WO | WO-2015186091 | A1 * | 12/2015 | ............... A61K 8/88 |
| WO | WO-2016005184 | A1 * | 1/2016 | ............... A61Q 5/00 |

OTHER PUBLICATIONS

Machine-assisted English translation for CN 106491392 A (Year: 2017).*
Research Disclosure (RD) 599035 A (Derwent abstract: Access No. 2014-J86818). (Year: 2014).*
Derwent English abstract for WO 2015/186091 A1. (Year: 2015).*
Croda ("The Use of Polyamides in Hair Care (oil) Compositions", Research Disclosure ("RD") 599035 (Feb. 2014)).*
Mintel; Anonymous: "Shampoo", Sep. 2017, Database GNPD [Online], XP055690172.
Mintel; Anonymous: "Shampoo", Feb. 2016, Database GNPD [Online], XP055690176.
Mintel; Anonymous: "Shampoo", Aug. 2013, Database GNPD [Online], XP055690189.
Mintel; Anonymous: "Hot Oil", Sep. 2011, Database GNPD [Online] XP055768204, Database accession No. 1639775.
Mintel; Anonymous: "5 Senses Hair & Body Enhancing Dry Oil", Nov. 2015, Database GNPD [Online] XP055768289, Database accession No. 3648677.
Mintel; Anonymous: "Hair Treatment & Styling Oil", Jan. 2017, Database GNPD [Online] XP055768290, Database accession No. 4475543.

* cited by examiner

*Primary Examiner* — Sin J Lee
(74) *Attorney, Agent, or Firm* — Lorenz & Kopf, LLP

(57) ABSTRACT

The present disclosure provides a silicone-free hair oil including one or more polyamides, one or more esters, one or more natural oils, one or more fatty alcohols, or a mixture thereof, and one or more hydrocarbons. The present disclosure also provides a method of using the silicone-free hair oil for the care of keratin fibres.

16 Claims, No Drawings

HAIR OILS FOR CONDITIONING KERATIN FIBRES

CROSS-REFERENCE TO RELATED APPLICATION

This application claims priority to German Patent Application No. 10 2018 221 937.0, filed Dec. 17, 2018, which is incorporated herein by reference in its entirety.

TECHNICAL FIELD

The present disclosure relates to cosmetic hair oils which comprise polyamides, esters and natural oils and are free from silicones, and use thereof for the care of keratin fibres.

BACKGROUND

Hair conditioners having a caring effect consist primarily of quats (quaternary ammonium compounds), silicone oils, fatty acids and polymer(s). For a few years now, the field of hair cosmetics has been developing hair oils that consist primarily of silicone oils. In addition, the hair oils are used as "leave-in products", that is to say the formulations remain in the hair without subsequent rinsing. The consumer thus saves time and water. The hair oils enjoy an advantageous sustainability from this point of view. The success of hair oils of this kind on the market has been very high.

The search is ongoing for new combinations that can ensure a high level of care, a perceptible care effect, and good stability. Within the scope of sustainability, increasing value is currently being placed on raw materials of plant origin or having good biodegradability. In this regard, silicone oils are a constant source of criticism. The good level of care, however, should not be compromised. The greatest difficulty in replacing silicone oils in hair oils lies in finding natural oils or natural raw materials that do not weigh down the hair or make it greasy.

Besides natural ambient influences, human hair is also exposed to a range of further, in particular cosmetic stresses. These stresses, which burden the hair, for example include hair dyeing and hair shaping, for example as a result of permanent waving. Cosmetic haircare agents are used in order to reduce the disadvantageous effects of the (ambient) influences that compromise the hair structure, but also in order to maintain and improve the natural hair structure. An essential active substance in many of these cosmetic agents is constituted by the organosilicon compounds, in particular the silicones such as trisiloxanes, which are exemplified by caring properties. The disadvantages of these silicones are the reduced penetration of active substances and auxiliaries into the hair caused by wetting of the hair surface, and the increased difficulty in styling the hair, likewise caused by the wetting of the hair surface. The provision of care agents that have a low silicone content or are free from silicone is therefore a relevant objective in the field of hair cosmetics.

The use of ester oils in hair-conditioning agents is described in international patent application WO 2010/063565 A1 (Henkel).

Document EP 2 623 088 A2 (Henkel) discloses haircare agents that contain at least one ester oil and at least one isoparaffin from the group of isodecane, isoundecane, isododecane, isotridecane and isotetradecane. Mixtures of ester oils and polymer quaternary ammonium compounds are additionally described, as are also combinations of both cosmetic agents.

SUMMARY

The object of the present disclosure is to provide cosmetic agents that make the co-use of organosilicon compounds, in particular silicones, superfluous and yet nevertheless maintain the performance range of the silicone-containing formulations. The weighing-down of the hair and the greasy condition of the treated hair often occurring with the use of silicones should be avoided. In particular, the object of the present disclosure is to enable the use of renewable raw materials in a silicone-free hair oil, while maintaining beneficial care and conditioning properties when the hair oil is used to treat hair fibres.

The object is achieved as contemplated herein by a silicone-free hair oil comprising:
 a) one or more polyamides,
 b) one or more esters,
 c) one or more natural oils and
 d) one or more hydrocarbons.

It has been found as contemplated herein that the combination of the above components gives rise to a hair oil that, in use, is advantageous in terms of silky hair feel, enhancement of shine/gloss, and beneficial smoothness, softness, and detangling.

In particular, hair oils that surprisingly provide improved care in respect of their detangling ability and combability, feel, shine and anti-frizz properties, without weighing down the hair, are produced. Especially by the use of *Ricinus Communis* (Castor) Seed Oil and/or isostearyl alcohol, the cosmetic agent as contemplated herein gains even more advantages in respect of its care properties. In addition, there is a strong sustainable aspect to the present disclosure as it enables the incorporation of plant oils based on renewable raw materials. In particular, the use of plant-based alkanes is possible, whereby the use of petrochemical constituents can be reduced or avoided.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

As component (a), the hair oil includes at least one polyamide. It should be understood by the skilled person that the polyamide is cosmetically acceptable, i.e. suitable for use in a cosmetic composition. Suitable polyamides include Polyamide-3 and Polyamide-8 (these being the INCI names). Polyamide-8 is a copolymer of ethylenediamine, neopentyl glycol and hydrogenated dilinoleic acid end-blocked with stearyl alcohol. Polyamide-3 is a polymer formed by the condensation of Dilinoleic Acid (q.v.), ethylenediamine, polypropylene glycol diamine end-capped with PEG/PPG-32/10 aminopropyl methyl ether. The polyamide component (a) is an oil-structuring polymer, which aids the formulation of the oil.

The hair oil may include only one polyamide or a mixture of two or more different polyamides. The hair oil may include a mixture of Polyamide-3 or Polyamide-8 with one or more other polyamides. Preferably, the hair oil includes Polyamide-8 with one or more other polyamides. More preferably, the only polyamide present is Polyamide-8.

A preferred commercial product to provide the Polyamide-8 is OleoCraft LP-20 supplied by Croda.

Suitably, the total amount of the or each polyamide ranges from about 0.5 to about 30 wt %, relative to the total weight of the hair oil. More suitably, the total amount of the or each polyamide ranges from about 1 to about 15 wt %, preferably from about 2 to about 10 wt %, more preferably from about 2 to about 5 wt %, relative to the total weight of the hair oil.

As component (b), the hair oils disclosed herein includes at least one ester.

The or each ester is suitably an alkoxylated alcohol.

Suitable esters are $C_6$-$C_{30}$ fatty acids with $C_2$-$C_{30}$ alcohols, diols or polyols.

Examples of fatty acid components used in the esters are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachinic acid, gadoleic acid, behenic acid and erucic acid and mixtures thereof. Examples of the alcohol components in the ester oils are isopropyl alcohol, caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and the technical mixtures thereof.

The monoesters of fatty acids with alcohols with 2 to 24 C atoms are preferred. A particularly preferred such monoester is isopropyl isostearate.

Another preferred ester (to be used alone or preferably in combination with one or more different esters) is neopentyl glycol diheptanoate.

The $C_6$-$C_{30}$ fatty acid may be unsaturated. A preferred ester of an unsaturated $C_6$-$C_{30}$ fatty acids with a $C_2$-$C_{30}$ alcohol is Heptyl Undecylenate.

Alternative esters for inclusion in the hair oils disclosed herein include isopropyl myristate (RILANIT® IPM), isononanoic acid $C_{16}$-$C_{18}$ alkyl esters (CETIOL® SN), 2-ethylhexyl palmitate (CEGESOFT® 24), stearic acid 2-ethylhexyl esters (CETIOL® 868), cetyloleate, glycerol tricaprylate, coconut fatty alcohol caprinate/caprylate (CETIOL® LC), n-butyl stearate, oleyl erucate (CETIOL® J 600), isopropyl palmitate (RILANIT® IPP), oleyl oleate (CETIOL®), lauric acid hexyl esters (CETIOL® A), di-n-butyl adipate (CETIOL® B), myristyl myristate (CETIOL® MM), cetearyl isononanoate (CETIOL® SN), oleic acid decyl esters (CETIOL® V).

A further preferred ester is PPG-3 Benzyl Ether Myristate.

A further preferred ester is a transester such as Shea Butter Ethyl Esters.

Suitably, the ester component in the hair oil is isopropyl isostearate, optionally in combination with one or more different esters. Preferably, isopropyl isostearate is present in combination with 2, 3 or 4 different esters.

Suitably, the ester component in the hair oil is neopentyl glycol diheptanoate, optionally in combination with one or more different esters. Preferably, neopentyl glycol diheptanoate is present in combination with 2, 3 or 4 different esters.

Suitably, the ester component in the hair oil is heptyl undecylenate, optionally in combination with one or more different esters. Preferably, heptyl undecylenate is present in combination with 2, 3 or 4 different esters.

Suitably, the ester component in the hair oil is PPG-3 Benzyl Ether Myristate, optionally in combination with one or more different esters. Preferably, PPG-3 Benzyl Ether Myristate is present in combination with 2, 3 or 4 different esters.

Suitably, the ester component in the hair oil is Shea Butter Ethyl Esters, optionally in combination with one or more different esters. Preferably, Shea Butter Ethyl Esters is present in combination with 2, 3 or 4 different esters.

Thus, the hair oil preferably comprises at least two esters selected from:
  Isopropyl Isostearate;
  Neopentyl Glycol Diheptanoate;
  Heptyl Undecylenate;
  PPG-3 Benzyl Ether Myristate; and
  Shea Butter Ethyl Esters.

The hair oil more preferably comprises at least three esters selected from:
  Isopropyl Isostearate;
  Neopentyl Glycol Diheptanoate;
  Heptyl Undecylenate;
  PPG-3 Benzyl Ether Myristate; and
  Shea Butter Ethyl Esters.

Suitable combinations of esters include PPG-3 Benzyl Ether Myristate and Neopentyl Glycol Diheptanoate, together with one or more of Shea Butter Ethyl Esters, Isopropyl Isostearate and Heptyl Undecylenate.

A particularly preferred combination of esters is:
  PPG-3 Benzyl Ether Myristate;
  Neopentyl Glycol Diheptanoate;
  Shea Butter Ethyl Esters; and
  Isopropyl Isostearate.

Another particularly preferred combination of esters is:
  PPG-3 Benzyl Ether Myristate;
  Neopentyl Glycol Diheptanoate; and
  Heptyl Undecylenate.

Alternative esters may be selected from the group of dicarboxylic acid esters, carbonate esters and diol esters. These are understood to be:
  dicarboxylic acid esters such as di-n-butyl adipate, di-(2-ethylhexyl) adipate, di-(2-ethylhexyl) succinate and di-isotridecylacelaate and
  diol esters such as ethylene glycol dioleate, ethylene glycol-di-isotridecanoate, propylene glycol-di(2-ethylhexanoate), propylene glycol-di-isostearate, propylene glycol-di-pelargonate, butanediol-di-isostearate, neopentyl glycol dicaprylate, and
  symmetrical, asymmetrical or cyclic esters of carbonic acid with fatty alcohols, such as glycerol carbonate or dicaprylyl carbonate (CETIOL® CC).

Suitable esters include carbonic acid with $C_6$-$C_{12}$ alkanols, in particular $C_7$-$C_9$ alkanols. The esters may particularly be symmetrical carbonic acid esters with alkanols, especially dicaprylyl carbonate (carbonic acid esters with n-octyl alcohol).

Further, suitable esters include tri-fatty acid esters of saturated and/or unsaturated linear and/or branched fatty acids with glycerol. Such esters may be selected from tri-fatty acid esters of saturated linear and/or branched $C_6$-$C_{12}$ carboxylic acids with glycerol. Linear $C_6$-$C_{12}$ carboxylic acids, in particular $C_8$-$C_{10}$ carboxylic acids, may be used. A suitable mixture is of tri-fatty acid esters of caprylic acid and capric acid with glycerol, for example in a ratio by weight of caprylic acid triglyceride to capric acid triglyceride of from about 3:1 to about 1:1.

Suitably, the total amount of the or each ester ranges from about 5 to about 60 wt %, relative to the total weight of the hair oil. Where the hair oil comprises only one ester, it should be understood that the total amount refers to the amount of the ester, relative to the total weight of the hair oil. Where the hair oil comprises more than one ester, it should be understood that the total amount refers to the combined amounts of the esters present, relative to the total weight of the hair oil. Preferably, the total amount of the or each ester ranges from about 5 to about 45 wt %, more preferably from about 10 to about 35 wt %, relative to the total weight of the hair oil.

As component (c), the hair oil disclosed herein includes at least one natural oil or a fatty alcohol, or a mixture thereof.

The or each natural oil may be selected from *Ricinus Communis* (Castor) Seed Oil, *Crambe Abyssinica* Seed Oil, amaranth seed oil, apricot kernel oil, argan oil, avocado oil, babassu oil, cottonseed oil, borage seed oil, camelina oil, safflower oil, peanut oil, pomegranate seed oil, grapefruit seed oil, hemp oil, hazelnut oil, elderberry seed oil, blackcurrant seed oil, jojoba oil, cocoa butter, linseed oil, Macadamia nut oil, corn oil, almond oil, manila oil, evening primrose oil, olive oil, orange oil, palm oil, peach kernel oil, rapeseed oil, rice bran oil, sea buckthorn fruit pulp oil, sea buckthorn seed oil, sesame oil, shea butter, soybean oil, sunflower oil, grape seed oil, walnut oil, wheat germ oil, wild rose oil, and the liquid parts of coconut oil.

The hair oil may include only one natural oil component or a mixture of two or more different natural oil components. The hair oil may include a mixture of *Ricinus Communis* (Castor) Seed Oil with one or more other natural oil components. More preferably, the only natural present is *Ricinus Communis* (Castor) Seed Oil.

As well as, or instead of, at least one natural oil, the hair oil includes at least one fatty alcohol as component (c). The fatty alcohol may be selected from isopropyl alcohol, caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and mixtures thereof. Preferably, component (c) comprises or consists of Isostearyl Alcohol. Component (c) may be a mixture of Isostearyl Alcohol and *Ricinus Communis* (Castor) Seed Oil.

Suitably, the total amount of component (c) ranges from about 0.1 to about 10 wt %, relative to the total weight of the hair oil. Preferably, the total amount of component (c) ranges from about 1 to about 8 wt %, preferably from about 2 to about 7 wt %, relative to the total weight of the hair oil.

As component (d), the hair oil disclosed herein includes at least one hydrocarbon. The hydrocarbons are preferably alkanes, suitably one or more alkanes selected from the group including isodecane, isoundecane, isododecane, isotridecane, and isotetradecane.

The hair oil may include only one alkane or a mixture of two or more different alkanes. The hair oil may include a mixture of isododecane with one or more other alkanes. Preferably, the hair oil includes isododecane present as the only alkane (falling under group (b)).

Suitably, the total amount of the or each hydrocarbon ranges from about 30 to about 80 wt %, relative to the total weight of the hair oil. More suitably, the total amount of the or each hydrocarbon ranges from about 40 to about 70 wt %, relative to the total weight of the hair oil.

An alkane that is particularly preferred as contemplated herein is commercially available under the name PUROLAN® IDD (Isododecane). The alkane may be present in a commercial product as a mixture with an ester. For example, a preferred commercial product according to the present disclosure is LexFeel® D5, which is a mixture of Neopentyl Glycol Diheptanoate and Isododecane.

The hair oil as contemplated herein can be adapted to the particular hair quality by the selection of suitable amounts of the components disclosed herein. Formulations for the treatment of fine, normal or thick hair can thus be obtained selectively.

By use of the hair oil as contemplated herein it is possible to dispense with organosilicon compounds, in particular silicones, in the hair oil. In the context of the present disclosure, "silicone-free" is taken to mean that the hair oil is free from organosilicon compounds, in particular free from silicones, trisiloxanes, and silicone oils.

Particularly preferably, the hair oil is applied by a dispenser onto the user's hand. Thus, the packaging is adapted based on that method of application, as would be well understood by the skilled person. The user then distributes the hair oil from their hand/hands to the hair length and tips. The user may spread the hair oil on their hand/hands before distribution. The user may pump the hair oil into their hand, so the dispenser may include a pump. The dispenser may also include a pipette to enable the oil to be dispensed from the dispenser to the hand. The dispenser may also include a droplet inlay.

The hair oil may alternatively be applied in the form of a sprayed oil and is sprayed onto the hair. The spray can be a pump spray, or the spraying can be achieved with the aid of propellants. Suitable propellants (propellant gases) are propane, propene, n-butane, iso-butane, iso-butene, n-pentane, pentene, iso-pentane, iso-pentene, methane, ethane, dimethylether, nitrogen, air, oxygen, nitrous oxide, 1,1,1,3-tetrafluoroethane, heptafluoro-n-propane, perfluoroethane, monochlorodifluoromethane, 1,1-difluoroethane, more specifically either individually or in combination. Hydrophilic propellant gases such as carbon dioxide, can also be used advantageously, if the proportion of hydrophilic gases is selected to be low and a lipophilic propellant gas (for example propane/butane) is present in excess. Propane, n-butane, isobutane, and mixtures of said propellant gases are particularly preferred. It has emerged that the use of n-butane as the sole propellant gas can be particularly preferred. Vessels made of metal (aluminium, tinplate, tin), protected or non-splintering plastic, or glass that is externally coated with plastic may be used as compressed gas containers; compressive strength and breaking strength, corrosion resistance, ease of filling, as well as aesthetic aspects, handling, printability, etc., play a role in their selection.

The present disclosure also relates to the use of the hair oil for the care of keratin fibres.

A further object of the present application is a method for the treatment of keratin fibres, exemplified in that a hair oil as contemplated herein is applied to the dried and/or damp keratin fibres.

The hair oil as contemplated herein is preferably used directly before, during or after an oxidative or surfactant hair treatment. In the context of the present disclosure, the expression "directly before the oxidative or surfactant hair treatment" is understood to mean an application that directly follows the oxidative or surfactant hair treatment, wherein the hair treatment agent as contemplated herein has been rinsed beforehand from the hair or preferably has been left on the hair, and the hair is preferably still wet.

The expression "after the oxidative or surfactant hair treatment" in the context of the present disclosure is understood to mean an application which either directly follows the oxidative or surfactant hair treatment, wherein the hair treatment agent as contemplated herein is applied to the preferably still wet, towel-dried hair once the agent with oxidative or surfactant effect has been rinsed out, or is applied to the dry or wet hair only after several hours or days. In both cases the hair treatment agent as contemplated herein can be rinsed out again after a reaction time of a few seconds up to about 45 minutes, or can remain fully on the hair.

A further object of the present application is the use of a hair oil as contemplated herein for the care of keratin fibres. What is claimed here in particular is the use of a cosmetic agent as contemplated herein
to improve the wet and dry combability of keratin fibres,
to improve the shine of keratin fibres,
to improve the feel of keratin fibres, Combability is understood as contemplated herein to mean both the combability of the wet fibres and the combability of the dry fibres. The combing work involved, or the force applied during the process of combing a collective of fibres, is used as a measure for combability. The measurement parameters can be assessed in a sensory manner by a person skilled in the art or can be quantified using measuring devices.

Besides the active substances described above, the hair oil as contemplated herein can contain further ingredients. The group of these further ingredients includes, in particular, the cosmetically effective active substances, auxiliaries and additives.

A first group of optional ingredients is formed by the additional substances that form oil bodies. Examples of these include di-n-alkyl ethers with a total of between 12 and 36 C atoms, for example:
di-n-alkyl ethers with a total between 12 and 36 C atoms, in particular 12 to 24 C atoms, such as di-noctyl ether, di-n-decyl ether, di-n-nonyl ether, di-n-undecyl ether, di-n-dodecyl ether, n-hexyl-noctyl ether, n-octyl-n-decyl ether, n-decyl-n-undecyl ether, n-undecyl-n-dodecyl ether and n-hexyl-n-undecyl ether and di-tert-butyl ether, di-iso-pentyl ether, di-3-ethyldecyl ether, tert.-butyl-n-octyl ether, iso-pentyl-n-octyl ether and 2-methyl-pentyl-n-octyl ether. The compounds 1,3-di-(2-ethyl-hexyl)-cyclohexane (CETIOL® S) and di-n-octyl ether (CETIOL® OE) obtainable as commercial products can be preferred.

The hair oil as contemplated herein can also contain fatty acid partial glycerides, that is to say monoglycerides, diglycerides and technical mixtures thereof, instead of component e) or as additional constituent. With use of technical products, small amounts of triglycerides may still be contained due to the production process. The partial glycerides preferably conform to the following formula,

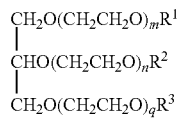

in which $R^1$, $R^2$ and $R^3$ independently of one another stand for hydrogen or for a linear or branched, saturated and/or unsaturated acyl group with from 6 to 22, preferably 12 to 18 carbon atoms, with the provision that at least one of these groups stands for an acyl group and at least of these groups stands for hydrogen. The sum (m+n+q) stands for 0 or numbers from 1 to 100, preferably for 0 or 5 to 25. $R^1$ preferably stands for an acyl group, and $R^2$ and $R^3$ preferably stand for hydrogen, and the sum (m+n+q) is 0. Typical examples are mono- and/or diglycerides based on caproic, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselinic acid, linoleic acid, linolenic acid, elaeostearic acid, arachinic acid, gadoleic acid, behenic acid and erucic acid and mixtures thereof. Oleic acid monoglycerides are preferably used.

Suitable active substances, auxiliaries and additives are in particular additional care substances. The agent for example can contain at least one protein hydrolysate and/or one of the derivatives thereof as care substance. Protein hydrolysates are product mixtures that are obtained by acid-catalysed, base-catalysed or enzymatically catalysed breakdown of proteins. The term "protein hydrolysates" is understood as contemplated herein to also mean total hydrolysates and also individual amino acids and derivatives thereof as well as mixtures of different amino acids. The molecular weight of the protein hydrolysates usable as contemplated herein lies between about 75, the molecular weight for glycine, and about 200,000 Daltons, and the molecular weight is preferably from about 75 to about 50,000 Daltons, and very particularly preferably from about 75 to about 20,000 Daltons.

As a care substance, the agent as contemplated herein can also contain at least one vitamin, a provitamin, a vitamin precursor and/or one of the derivatives thereof. Here, vitamins, provitamins and vitamin precursors that are usually assigned to the groups A, B, C, E, F and H are preferred.

Similarly to the addition of glycerol and/or propylene glycol, the addition of panthenol increases the flexibility of the polymer film formed with application of the agent as contemplated herein.

As a care substance, the agents as contemplated herein can also contain at least one plant extract, but also monosaccharides or oligosaccharides and/or lipids.

The hair oil disclosed herein may also include a perfume. Suitably, a perfume is included in an amount ranging from about 0.1 to about 0.8% by weight, preferably from about 0.2 to about 0.6% by weight, relative to the weight of the hair oil.

Particularly preferred hair oils as contemplated herein are preferably formulated as application mixtures with a low water content. The water content of preferred hair oils, in relation to the total weight of said hair oils, is less than about 10% by weight, preferably less than about 5.0% by weight, particularly preferably less than about 1.0% by weight, and in particular less than about 0.1% by weight, wherein very particularly preferred hair oils contain no water.

The hair oil disclosed herein may have any viscosity that renders the hair oil suitable for dispensing from the packaging to the user's hand. Viscosity of the hair oil disclosed herein may be measured in centipoise (cps). The hair oil disclosed herein may have a viscosity in the range of about 0.8 cps to about 500,000 cps. In one example, a hair oil as disclosed herein is offered as a dispensable liquid with a viscosity in the range of about 300 to about 5,000 cps, such as from about 1,000 cps to about 4,000 cps.

Methods

The present specification is also directed to a method for using a hair oil as contemplated herein. The method includes applying the hair oil as disclosed herein to the hair. The method includes dispensing the hair oil as disclosed herein onto the user's hand, and from the user's hand onto the hair. The method may additionally include rubbing the hair. The method may include the user spreading the hair oil on their hand or hands before application to the hair.

The method for using a hair oil as disclosed herein may also include additional optional steps. In one example, such steps may include air drying the hair, drying the hair using heat, styling the hair, and any other suitable step that is known to an individual skilled in the art of hair treatment.

The present disclosure may be exemplified by the following numbered statements.

1. A silicone-free hair oil comprising:
   a) one or more polyamides,
   b) one or more esters,
   c) one or more natural oils, or one or more fatty alcohols, or a mixture thereof, and
   d) one or more hydrocarbons.
2. A hair oil according to statement 1, wherein the polyamide is Polyamide-3 or Polyamide-8.
3. A hair oil according to statement 1, wherein the polyamide is Polyamide-8.
4. A hair oil according to statement 1, wherein the polyamide is Polyamide-3.
5. A hair oil according to any preceding statement, wherein the total amount of the or each polyamide ranges from about 0.5 to about 30 wt %, relative to the total weight of the hair oil.
6. A hair oil according to any preceding statement, wherein the total amount of the or each polyamide ranges from about 1 to about 15 wt %,
7. A hair oil according to any preceding statement, wherein the total amount of the or each polyamide ranges from about 2 to about 10 wt %.
8. A hair oil according to any preceding statement, wherein the total amount of the or each polyamide ranges from about 2 to about 5 wt %, relative to the total weight of the hair oil.
9. A hair oil according to any preceding statement, wherein the or each ester is selected from esters of $C_6$-$C_{30}$ fatty acids with $C_2$-$C_{30}$ alcohols, diols or polyols.
10. A hair oil according to any preceding statement, wherein the ester comprises or consists of isopropyl isostearate.
11. A hair oil according to any preceding statement, wherein the ester comprises or consists of neopentyl glycol diheptanoate.
12. A hair oil according to any preceding statement, wherein the ester comprises or consists of PPG-3 Benzyl Ether Myristate.
13. A hair oil according to any preceding statement, wherein the ester comprises or consists of Shea Butter Ethyl Esters.
14. A hair oil according to any preceding statement, wherein the ester comprises or consists of Heptyl Undecylenate.
15. A hair oil according to any preceding statement, wherein the ester comprises or consists of PPG-3 Benzyl Ether Myristate and Neopentyl Glycol Diheptanoate.
16. A hair oil according to any preceding statement, wherein the ester is a mixture of PPG-3 Benzyl Ether Myristate, Shea Butter Ethyl Esters, Isopropyl Isostearate and Neopentyl Glycol Diheptanoate.
17. A hair oil according to any one of statements 1 to 15, wherein the ester is a mixture of PPG-3 Benzyl Ether Myristate, Heptyl Undecylenate and Neopentyl Glycol Diheptanoate.
18. A hair oil according to any preceding statement, wherein the total amount of the or each ester ranges from about 5 to about 60 wt %, relative to the total weight of the hair oil.
19. A hair oil according to any preceding statement, wherein the total amount of the or each ester ranges from about 5 to about 45 wt %.
20. A hair oil according to any preceding statement, wherein the total amount of the or each ester ranges from about 10 to about 35 wt %, relative to the total weight of the hair oil.
21. A hair oil according to any preceding statement, wherein the or each natural oil is selected from *Ricinus Communis* (Castor) Seed Oil, *Crambe Abyssinica* Seed Oil, amaranth seed oil, apricot kernel oil, argan oil, avocado oil, babassu oil, cottonseed oil, borage seed oil, camelina oil, safflower oil, peanut oil, pomegranate seed oil, grapefruit seed oil, hemp oil, hazelnut oil, elderberry seed oil, currant seed oil, jojoba oil, cocoa butter, linseed oil, Macadamia nut oil, maize germ oil, almond oil, marula oil, evening primrose oil, olive oil, orange oil, palm oil, peach seed oil, rapeseed oil, rice oil, sea buckthorn fruit pulp oil, sea buckthorn seed oil, sesame oil, shea butter, soybean oil, sunflower oil, grape seed oil, walnut oil, wheat germ oil, wild rose oil, the liquid parts of coconut oil and mixtures thereof
22. A hair oil according to any preceding statement, wherein component (c) comprises or consists of *Ricinus Communis* (Castor) Seed Oil.
23. A hair oil according to any preceding statement, wherein component (c) consists of *Ricinus Communis* (Castor) Seed Oil.
24. A hair oil according to any preceding statement, wherein the or each fatty alcohol is selected from isopropyl alcohol, caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and mixtures thereof
25. A hair oil according to any preceding statement, wherein component (c) comprises or consists of Isostearyl Alcohol.
26. A hair oil according to any one of statements 1 to 24, wherein component (c) consists of Isostearyl Alcohol.
27. A hair oil according to any preceding statement, wherein the total amount of component (c) ranges from about 0.1 to about 10 wt %, relative to the total weight of the hair oil.
28. A hair oil according to any preceding statement, wherein the total amount of component (c) ranges from about 1 to about 8 wt %.
29. A hair oil according to any preceding statement, wherein the total amount of component (c) ranges from about 2 to about 7 wt %, relative to the total weight of the hair oil.
30. A hair oil according to any preceding statement, wherein the or each hydrocarbon is an alkane.
31. A hair oil according to any preceding statement, wherein the hydrocarbon is selected from isodecane, isoundecane, isododecane, isotridecane, isotetradecane, C12-17 Alkane and mixtures thereof
32. A hair oil according to any preceding statement, wherein the hydrocarbon comprises or consists of isododecane.
33. A hair oil according to any preceding statement, wherein the hydrocarbon comprises or consists of C12-17 Alkane.
34. A hair oil according to any preceding statement, wherein the hydrocarbon is a mixture of isododecane and C12-17 Alkane.

35. A hair oil according to any preceding statement, wherein the total amount of the or each hydrocarbon ranges from about 30 to about 80 wt %, relative to the total weight of the hair oil.
36. A hair oil according to any preceding statement, wherein the total amount of the or each hydrocarbon ranges from about 40 to about 70 wt %, relative to the total weight of the hair oil.
37. A cosmetic product comprising the hair oil according to any preceding statement.
38. A cosmetic product according to statement 37, wherein the product comprises a pump dispenser
39. A cosmetic product according to statement 37, wherein the product comprises a pipette.
40. A cosmetic product according to statement 37, wherein the product comprises a droplet inlay.
41. Use of a hair oil or a cosmetic product according to any preceding statement for the care of hair fibres.
42. A method for using a hair oil as defined in any one of statements 1 to 36, or a cosmetic product according to any one of statements 37 to 40, the method comprising applying the hair oil to the hair.
43. A method according to statement 42, wherein the application comprises dispensing the cosmetic agent onto the user's hand, followed by application of the cosmetic agent from the user's hand to the hair.

EXAMPLES

All specified amounts relate to parts by weight. The following formulations were provided with the use of known production methods.

Example 1

| Ingredient (INCI Name) | wt % |
|---|---|
| Polyamide-8 | 4.0 |
| PPG-3 Benzyl Ether Myristate | 20.0 |
| Shea Butter Ethyl Esters | 1.0 |
| Isopropyl Isostearate | 10.0 |
| *Ricinus Communis* (Castor) Seed Oil | 5.0 |
| Isododecane | 52.2 |
| Neopentyl Glycol Diheptanoate | 7.8 |
| | 100 |

Example 2

| Ingredient (INCI Name) | wt % |
|---|---|
| Polyamide-8 | 4.0 |
| PPG-3 Benzyl Ether Myristate | 10.0 |
| Heptyl Undecylenate | 5.0 |
| C12-17 Alkane | 45.0 |
| Isostearyl Alcohol | 5.0 |
| Isododecane | 21.3 |
| Neopentyl Glycol Diheptanoate | 9.4 |
| Perfume | 0.3 |
| | 100 |

For example:
SP Oleocraft LP-20 MBAL-PA-(MV) can be used as Polyamide-8;
Crodamol STS-LQ-(MH) can be used as PPG-3 Benzyl Ether Myristate;
Lipex Shea Light can be used as Shea Butter Ethyl Esters;
CRODAMOL IPIS-LQ-(MV) can be used as Isopropyl Isostearate;
Castor oil DAB/Ph.Eur. can be used as *Ricinus Communis* (Castor) Seed Oil;
PUROLAN IDD can be used as Isododecane; and
LexFeel D5, which is a mixture of Neopentyl Glycol Diheptanoate and Isododecane, can be used.

The exemplified hair oils were found to be advantageous in terms of silky hair feel, enhancement of shine/gloss, and beneficial smoothness, softness, and detangling.

It will be appreciated that the present disclosure may be modified within the scope of the appended claims.

Additionally, while at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A cosmetic composition comprising:
one or more polyamides;
one or more esters, wherein the one or more esters is a mixture of PPG-3 Benzyl Ether Myristate, Shea Butter Ethyl Esters, Isopropyl Isostearate and Neopentyl Glycol Diheptanoate, or a mixture of PPG-3 Benzyl Ether Myristate, Heptyl Undecylenate and Neopentyl Glycol Diheptanoate;
one or more natural oils, one or more fatty alcohols, or a mixture thereof; and
one or more hydrocarbons,
wherein the composition is a silicone-free leave-in hair oil,
wherein the silicone-free hair oil is a dispensable liquid having a viscosity of from about 0.8 to about 500,000 cps.

2. The cosmetic composition according to claim 1, wherein the cosmetic composition includes no water or less than 0.1 wt % of water, relative to the total weight of the cosmetic composition.

3. The cosmetic composition according to claim 1, wherein the cosmetic composition comprises:
a) 1 to 15 wt % of the one or more polyamides, relative to the total weight of the cosmetic composition;
b) 5 to 45 wt % of the one or more esters, relative to the total weight of the cosmetic composition;
c) 0.1 to 8 wt % of the one or more natural oils, one or more fatty alcohols, or mixture thereof, relative to the total weight of the cosmetic composition; and
d) 40 to 70 wt % of the one or more hydrocarbons, relative to the total weight of the cosmetic composition.

4. The cosmetic composition according to claim 1, wherein the cosmetic composition comprises:
a) 2 to 10 wt % of the one or more polyamides, relative to the total weight of the cosmetic composition;
b) 10 to 35 wt % of the one or more esters, relative to the total weight of the cosmetic composition;

c) 2 to 7 wt % of the one or more natural oils, one or more fatty alcohols, or mixture thereof, relative to the total weight of the cosmetic composition; and d) 40 to 70 wt % of the one or more hydrocarbons, relative to the total weight of the cosmetic composition.

5. The cosmetic composition according to claim 1, wherein the one or more natural oils is selected from the group consisting of *Ricinus Communis* (Castor) Seed Oil, *Crambe Abyssinica* Seed Oil, amaranth seed oil, apricot kernel oil, argan oil, avocado oil, babassu oil, cottonseed oil, borage seed oil, camelina oil, safflower oil, peanut oil, pomegranate seed oil, grapefruit seed oil, hemp oil, hazelnut oil, elderberry seed oil, currant seed oil, jojoba oil, cocoa butter, linseed oil, Macadamia nut oil, maize germ oil, almond oil, manila oil, evening primrose oil, olive oil, orange oil, palm oil, peach seed oil, rapeseed oil, rice oil, sea buckthorn fruit pulp oil, sea buckthorn seed oil, sesame oil, shea butter, soybean oil, sunflower oil, grape seed oil, walnut oil, wheat germ oil, wild rose oil, the liquid parts of coconut oil, and mixtures thereof.

6. The cosmetic composition according to claim 1, wherein the one or more fatty alcohols is selected from the group consisting of caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol, and mixtures thereof.

7. The cosmetic composition according to claim 1, wherein the one or more natural oils, one or more fatty alcohols, or mixture thereof comprises *Ricinus Communis* (Castor) Seed Oil or Isostearyl Alcohol.

8. The cosmetic composition according to claim 1, wherein the cosmetic composition comprises:
a) 2 to 5 wt % of the one or more polyamides, relative to the total weight of the cosmetic composition;
b) 10 to 35 wt % of the one or more esters, relative to the total weight of the cosmetic composition;
c) 2 to 7 wt % of the one or more natural oils, one or more fatty alcohols, or mixture thereof, relative to the total weight of the cosmetic composition; and
d) 40 to 70 wt % of the one or more hydrocarbons, relative to the total weight of the cosmetic composition.

9. The cosmetic composition according to claim 8, wherein the one or more natural oils, one or more fatty alcohols, or mixture thereof includes Isostearyl Alcohol, *Ricinus Communis* (Castor) Seed Oil, or mixtures thereof.

10. The cosmetic composition according to claim 1, wherein:
the one or more polyamides is Polyamide-3 or Polyamide-8, and the one or more hydrocarbons is an alkane.

11. The cosmetic composition according to claim 10, wherein the one or more hydrocarbons is selected from the group consisting of isodecane, isoundecane, isododecane, isotridecane, isotetradecane, $C_{12}$-$C_{17}$Alkane, and mixtures thereof.

12. The cosmetic composition according to claim 1, wherein:
the one or more polyamides is Polyamide-3 or Polyamide-8, and
the one or more hydrocarbon comprises isododecane, a $C_{12}$-$C_{17}$Alkane, or a mixture of isododecane and $C_{12}$-$C_{17}$Alkane.

13. The cosmetic composition according to claim 1 wherein the cosmetic composition comprises:
a) 0.5 to 30 wt % of the one or more polyamides, relative to the total weight of the cosmetic composition;
b) 5 to 60 wt % of the one or more esters, relative to the total weight of the cosmetic composition;
c) 0.1 to 10 wt % of the one or more natural oils, one or more fatty alcohols, or a mixture thereof, relative to the total weight of the cosmetic composition; and
d) 30 to 80 wt % of the one or more hydrocarbons, relative to the total weight of the cosmetic composition.

14. The cosmetic composition according to claim 13, wherein the cosmetic composition comprises:
a) 2 to 5 wt % of the one or more polyamides, relative to the total weight of the cosmetic composition;
b) 10 to 35 wt % of the one or more esters, relative to the total weight of the cosmetic composition;
c) 2 to 7 wt % of the one or more natural oils, one or more fatty alcohols, or mixture thereof, relative to the total weight of the cosmetic composition; and
d) 40 to 70 wt % of the one or more hydrocarbons, relative to the total weight of the cosmetic composition.

15. A method for caring for hair fibres, the method comprising applying a cosmetic composition according to claim 1 to the hair fibres and allowing the cosmetic composition to remain in the hair fibres without subsequent rinsing before air drying the hair fibres, drying the hair fibres using heat, or styling the hair fibres.

16. A silicone-free hair oil comprising:
(a) from about 2 to about 5 wt % of Polyamide-8;
(b) from about 10 to about 45 wt % of a plurality of esters including PPG-3 Benzyl Ether Myristate, Neopentyl Glycol Diheptanoate, and at least one ester selected from the group consisting of Shea Butter Ethyl Esters, Isopropyl Isostearate, and Heptyl Undecylenate;
(c) from about 2 to about 7 wt % of Isostearyl Alcohol, *Ricinus Communis* (Castor) Seed Oil, or mixtures thereof; and
(d) from about 40 to about 70 wt % of Isododecane, $C_{12}$-$C_{17}$Alkane, or mixtures thereof.

* * * * *